United States Patent
Watanabe (10) Patent No.: US 11,325,880 B2
(45) Date of Patent: May 10, 2022

(54) METHOD FOR PRODUCING BIFUNCTIONAL COMPOUND HAVING NORBORNANE SKELETON

(71) Applicant: Mitsubishi Gas Chemical Company, Inc., Chiyoda-ku (JP)

(72) Inventor: Taku Watanabe, Yokohama (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 16/973,134

(22) PCT Filed: Jun. 17, 2019

(86) PCT No.: PCT/JP2019/023839
§ 371 (c)(1),
(2) Date: Dec. 8, 2020

(87) PCT Pub. No.: WO2019/244822
PCT Pub. Date: Dec. 26, 2019

(65) Prior Publication Data
US 2021/0253510 A1 Aug. 19, 2021

(30) Foreign Application Priority Data
Jun. 18, 2018 (JP) .............................. JP2018-115434

(51) Int. Cl.
*C07C 45/50* (2006.01)
*C07C 67/36* (2006.01)
*C07C 67/313* (2006.01)

(52) U.S. Cl.
CPC ........ *C07C 67/313* (2013.01); *C07C 2603/86* (2017.05)

(58) Field of Classification Search
CPC .................................. C07C 45/50; C07C 67/36
See application file for complete search history.

(56) References Cited

U.S. PATENT DOCUMENTS

| 9,975,843 B2 * | 5/2018 | Motoi .................. C07C 47/347 |
| 2017/0088504 A1 | 3/2017 | Motoi et al. |

FOREIGN PATENT DOCUMENTS

| JP | 58-21638 A | 2/1983 |
| JP | 59-110643 A | 6/1984 |
| JP | 5-97769 A | 4/1993 |
| JP | 2000-143573 A | 5/2000 |
| WO | WO 2015/147242 A1 | 10/2015 |

OTHER PUBLICATIONS

International Search Report dated Aug. 27, 2019 in PCT/JP2019/023839 filed Jun. 17, 2019, 2 pages.
Tijani, J., et al., "Rhodium-catalyzed hydroformylation of olefins: Effect of [bis(2, 4-di-tert-butyl) pentaerythritol] diphosphite (alkanox P-24) on the regioselectivity of the reaction", Journal of Organometallic Chemistry, vol. 692, 2007, pp. 3492-3497.

* cited by examiner

*Primary Examiner* — Sikarl A Witherspoon
(74) *Attorney, Agent, or Firm* — Oblon, McClelland, Maier & Neustadt, L.L.P.

(57) ABSTRACT

The present invention provides a method for producing a bifunctional compound having a norbornane skeleton, the method comprising a step of hydroformylating a compound having an olefin with carbon monoxide and hydrogen, wherein the molar ratio of the carbon monoxide to the hydrogen during the reaction is 55/45 or more and 95/5 or less in the hydroformylating step.

5 Claims, 4 Drawing Sheets

METHOD FOR PRODUCING BIFUNCTIONAL COMPOUND HAVING NORBORNANE SKELETON

TECHNICAL FIELD

The present invention relates to a method for producing a bifunctional compound having a norbornane skeleton useful as coating additives, adhesives, starting materials of resin, and the like. Also, the present invention relates to a production method for preventing a monofunctional compound having a norbornane skeleton from being by-produced.

BACKGROUND ART

It is known that a bifunctional compound having a norbornane skeleton exhibits excellent characteristics when used as adhesives or starting materials of resin. As a method for producing a bifunctional compound having a norbornane skeleton, for example, Patent Literature 1 describes that a bifunctional compound having a norbornane skeleton can be obtained through a hydroformylation reaction of a compound having a corresponding olefin.

CITATION LIST

Patent Literature

Patent Literature 1: International Publication No. WO 2015/147242

SUMMARY OF INVENTION

Technical Problem

A hydroformylation reaction is performed by reacting a compound having an olefin with an oxo gas, in presence of a catalyst containing rhodium or cobalt. The oxo gas for use as a starting material in the hydroformylation reaction is usually a gas having a controlled molar ratio between carbon monoxide and hydrogen of 50:50, because the hydroformylation reaction is represented by the following reaction formula. In the reaction between the oxo gas and the compound having an olefin, however, a certain amount of byproduct formed by hydrogenation of the compound having an olefin, is generated along with production of a bifunctional compound having a norbornane skeleton.

Also, use of the bifunctional compound having a norbornane skeleton thus produced as a starting material of a polymer causes the hydrogenated byproduct to inhibit a reaction into a polymer. However, both of the bifunctional compound having a norbornane skeleton and the hydrogenated byproduct have high viscosity and high boiling point, so that it is difficult to separate the hydrogenated byproduct from the bifunctional compound having a norbornane skeleton by simple distillation or thin film distillation. Also, although use of distillation purification with a high number of stages for separating the hydrogenated byproduct from the bifunctional compound having a norbornane skeleton can achieve a specified separation, the yield is worsened. It is therefore difficult to say that use of distillation purification with a high number of stages is an economical method. From these circumstances, a synthesis method capable of inhibiting generation of the hydrogenated byproduct in the hydroformylation reaction is desired.

In order to solve the problem, the present invention provides a method for producing a bifunctional compound having a norbornane skeleton which method is capable of preventing generation of a hydrogenated byproduct in the hydroformylation reaction.

Solution to Problem

The present inventors have found that increase in molar quantity of carbon monoxide than hydrogen by a predetermined value or more in the composition of an oxo gas (mixed gas of carbon monoxide and hydrogen) during hydroformylation reaction results in decrease in formation of the hydrogenated byproduct, so that the present invention has been accomplished.

In other words, the present invention is as follows.

[1] A method for producing a compound represented by formula (1), comprising a step of hydroformylating a compound represented by formula (2) with carbon monoxide and hydrogen, wherein a molar ratio of the carbon monoxide to the hydrogen during reaction is 55/45 or more and 95/5 or less in the hydroformylating step:

wherein $R_1$ represents $COOCH_3$, $COOC_2H_5$, $COOC_3H_7$, $COOC_4H_9$, $CHO$, $OCOCH_3$ or $OH$; $R_2$ represents $H$, $CH_3$ or $C_2H_5$; and n is 0 or 1:

wherein $R_1$, $R_2$ and n are the same as defined in the formula (1).

[2] The production method according to [1], wherein the compound represented by the formula (1) obtained in the hydroformylating step has a content of a compound represented by formula (3) of 1 mol % or less:

wherein $R_1$, $R_2$ and n are the same as defined in the formula (1).

[3] The production method according to [1] or [2], wherein the hydroformylating step uses 0.1 to 60 micromoles of a rhodium compound per mole of the compound represented by the formula (2), and 300 to 10000 moles of an organic phosphorus compound per mole of a rhodium atom in the rhodium compound.

Advantageous Effects of Invention

According to the production method of the present invention, a bifunctional compound having a norbornane skeleton useful as coating additives, adhesives, starting materials of resin, and the like can be produced by an industrially advantageous method with generation of a hydrogenated byproduct inhibited.

DESCRIPTION OF EMBODIMENTS

Embodiments of the present invention (hereinafter also referred to as "present embodiment") will be described in detail below. The following embodiments are intended to illustrate the present invention but are not intended to limit the present invention to the following. The present invention may be appropriately modified in the scope of the present invention.

[Production Method of Bifunctional Compound Having Norbornane Skeleton]

The production method in the present embodiment is a method for producing a compound represented by a formula (1) (hereinafter, also referred to as "bifunctional compound having a norbornane skeleton"). The production method in the present embodiment comprises a step of hydroformylating a compound represented by a formula (2) (hereinafter, also referred to as "compound having a norbornene skeleton") with carbon monoxide and hydrogen (hereinafter, carbon monoxide and hydrogen together are called as "oxo gas") (hereinafter, also referred to as "hydroformylating step"). In the hydroformylating step, the molar ratio of the carbon monoxide to the hydrogen during the reaction is 55/45 or more and 95/5 or less:

(1)

wherein $R_1$ represents $COOCH_3$, $COOC_2H_5$, $COOC_3H_7$, $COOC_4H_9$, CHO, $OCOCH_3$ or OH, $R_2$ represents H, $CH_3$ or $C_2H_5$; n is 0 or 1; and $R_1$ is preferably $COOCH_3$ or CHO:

(2)

wherein $R_1$, $R_2$ and n are the same as defined in the formula (1).

[Bifunctional Compound Having a Norbornane Skeleton]

The bifunctional compound having a norbornane skeleton in the present embodiment exhibits excellent characteristics when used as adhesives and starting materials of resin. Herein, "bifunctional compound" refers to a compound having at least two reactive functional groups, and the bifunctional compound having a norbornane skeleton in the present embodiment has two reactive functional groups, i.e., —CHO and $R_1$, which bind to the norbornane skeleton. $R_2$ is a non-reactive functional group.

The bifunctional compound having a norbornane skeleton is not particularly limited as long as it is a bifunctional compound having a norbornane skeleton represented by the formula (1), and it is preferably a bifunctional compound having a norbornane skeleton having 8 to 20 carbon atoms.

[Compound Having a Norbornene Skeleton]

The compound having a norbornene skeleton is not particularly limited as long as it is a compound having a norbornene skeleton represented by the formula (2), and it is preferably a monoolefin having 7 to 19 carbon atoms.

A compound having a norbornene skeleton may be produced, for example, by performing a Diels-Alder reaction of a monoolefin and dicyclopentadiene.

Examples of the monoolefin for use in the Diels-Alder reaction include methyl (meth)acrylate, ethyl (meth)acrylate, propyl (meth)acrylate, butyl (meth)acrylate, (meth) acrolein and ethyl acrolein. In particular, methyl (meth) acrylate, ethyl (meth)acrylate, (meth)acrolein and ethyl acrolein are preferred. Herein, "(meth)acrylate" includes both of "methacrylate" and "acylate", and "(meth)acrolein" includes both of "methacrolein" and "acrolein".

The dicyclopentadiene for use in the Diels-Alder reaction in the present embodiment is preferably one having high purity, and containment of butadiene, isoprene, or the like is preferably minimized. The purity of dicyclopentadiene is more preferably 90% or more, still more preferably 95% or more. As it is known that dicyclopentadiene is depolymerized under heating conditions to produce cyclopentadiene (so-called monocyclopentadiene), cyclopentadiene may be used instead of dicyclopentadiene. It is considered that among compounds having a norbornene skeleton represented by the formula (2), a compound wherein n is 1 is formed substantially through a compound having a norbornene skeleton having 7 to 14 carbon atoms represented by the following formula (4) (product of first-stage Diels-Alder reaction). Thus, it is considered that the formed monoolefin of the formula (4) as a new dienophile compound causes a Diels-Alder reaction with cyclopentadiene present in the reaction system (second-stage Diels-Alder reaction), so that a compound wherein n is 1, among compounds having a norbornene skeleton represented by the formula (2), is formed.

(4)

wherein $R_1$ and $R_2$ are the same as defined in the formula (1).

In order to efficiently proceed the two-stage Diels-Alder reaction, it is important that cyclopentadiene be present in a reaction system. The reaction temperature, therefore, is preferably 100° C. or more, more preferably 120° C. or more, particularly preferably 130° C. or more. On the other hand, it is preferable that the reaction be performed at a temperature of 250° C. or less in order to prevent generation of byproducts having a high-boiling point. Also, as reaction solvent, hydrocarbons, alcohols, esters, etc., may be used, and aliphatic hydrocarbons having 6 or more carbon atoms, cyclohexane, toluene, xylene, ethylbenzene, mesitylene, propanol, butanol, etc., are suitably used.

As the Diels-Alder reaction method, various reaction methods may be employed, including a batch method with a tank-type reaction vessel or the like, a semi-batch method with a tank-type reaction vessel under reaction conditions in which reactants or reactant solution are supplied, and a continuous flow method with a pipe-type reaction vessel in which reactants flow under reaction conditions.

A reaction product obtained in the Diels-Alder reaction may be directly used as a starting material in the subsequent hydroformylation reaction, or may be subjected to purification by a method such as distillation, extraction, and crystal precipitation, and then supplied to the subsequent step.

[Hydroformylating Step]

The hydroformylating step in the present embodiment is preferably performed in the presence of a rhodium compound and an organic phosphorus compound, though not particularly limited. The rhodium compound for use is not particularly limited as long as it is a compound which forms a complex with an organic phosphorus compound to exhibit hydroformylation activity in the presence of carbon monoxide and hydrogen. Examples of the rhodium compound include rhodium acetyl acetonate dicarbonyl (hereinafter, described as $Rh(acac)(CO)_2$), $Rh_2O_3$, $Rh_4(CO)_{12}$, $Rh_6(CO)_{16}$, and $Rh(NO_3)_3$. The rhodium compound may be introduced as a precursor together with an organic phosphorus compound into a reaction mixture so as to form a rhodium metal hydride carbonyl phosphorus complex having a catalyst activity in a reaction vessel, or may be prepared into a rhodium metal hydride carbonyl phosphorus complex in advance, which is introduced into a reaction vessel.

The amount of the rhodium compound used is preferably 0.1 to 60 micromoles, more preferably 0.1 to 30 micromoles, still more preferably 0.2 to 20 micromoles, further more preferably 0.5 to 10 micromoles, per mole of the compound having a norbornene skeleton as reactant of the hydroformylation reaction. When the amount of the rhodium compound used is less than 60 micromoles per mole of the compound having a norbornene skeleton, the cost of rhodium catalyst can be reduced without providing facilities for collecting and recycling the rhodium complex. As a result, the economic burden on the facilities for collecting and recycling can be reduced.

The organic phosphorus compound for use in the hydroformylating step in the present embodiment is not particularly limited as long as it can form a catalyst of the hydroformylation reaction with a rhodium compound. Examples of the organic phosphorus compound include a phosphine represented by a general formula $P(-R_1)(-R_2)(-R_3)$, or a phosphite represented by $P(-OR_1)(-OR_2)(-OR_3)$. Specific examples of $R_1$, $R_2$ and $R_3$ include an aryl group which may be substituted with an alkyl group or alkoxy group having 1 to 4 carbon atoms, and an alicyclic alkyl group which may be substituted with an alkyl group or alkoxy group having 1 to 4 carbon atoms, and triphenyl phosphine and triphenyl phosphite are suitably used.

The amount of the organic phosphorus compound used is preferably 300 to 10000 moles, more preferably 500 to 10000 moles, still more preferably 700 to 5000 moles, further more preferably 900 to 2000 moles, per mole of the rhodium atom in the rhodium compound. When the amount of the organic phosphorus compound used is more than 300 moles per mole of the rhodium atom in the rhodium compound, the stability of a rhodium metal hydride carbonyl phosphorus complex as a catalyst activator is hardly impaired, so that delay in the progress of the reaction can be suppressed. When the amount of the organic phosphorus compound used is less than 10000 moles per mole of the rhodium atom in the rhodium compound, increase in the cost of the organic phosphorus compound can be suppressed.

Although the hydroformylating step in the present embodiment may be performed without use of a solvent, the step can be further suitably performed in the presence of a solvent inactive to the reaction. The solvent is not particularly limited as long as it can dissolve at least a part of the compound having a norbornene skeleton represented by the formula (2). In addition, it is preferable that the solvent can dissolve at least a part of the rhodium compound and the organic phosphorus compound. Examples of the solvent include hydrocarbons such as aliphatic hydrocarbons, alicyclic hydrocarbons and aromatic hydrocarbons; esters such as aliphatic esters, alicyclic esters and aromatic esters; alcohols such as aliphatic alcohols and alicyclic alcohols; and aromatic halides. Among these, hydrocarbons are suitably used, and, in particular, alicyclic hydrocarbons and aromatic hydrocarbons are suitably used.

The temperature at which the hydroformylation reaction in the present embodiment is performed is, for example, preferably 40° C. to 160° C., more preferably 80° C. to 140° C., though not particularly limited. With a reaction temperature of 40° C. or more, a sufficient reaction rate can be obtained, so that the compound having a norbornene skeleton as a starting material is prevented from remaining. With a reaction temperature of 160° C. or less, generation of byproducts derived from the compound having a norbornene skeleton as a starting material or reaction products is suppressed, so that deterioration in the reaction performance can be prevented.

In the hydroformylating step in the present embodiment, the reaction is performed in the presence of carbon monoxide (hereinafter, also referred to as "CO") and hydrogen (hereinafter, also referred to as "$H_2$"), preferably under pressure. CO and $H_2$ may be separately introduced into a reaction system, or may be mixed to prepare an oxo gas in advance for introduction into a reaction system.

The molar ratio of CO to $H_2$ (=$CO/H_2$ molar ratio) during reaction is 55/45 or more and 95/5 or less, preferably 60/40 or more and 90/10 or less, more preferably 70/30 or more and 80/20 or less. With a $CO/H_2$ molar ratio in such a range, the reaction activity of the hydroformylation reaction and the selectivity of the target aldehyde are improved. In particular, with a $CO/H_2$ molar ratio of 55/45 or more, generation of the hydrogenated byproducts can be inhibited due to reduction in the partial pressure of hydrogen in the reaction system. Since CO and $H_2$ introduced into the reaction system decrease along with progress of the reaction, use of a mixed gas of CO and $H_2$ prepared in advance results in easiness of reaction control in some cases.

The reaction pressure in the hydroformylation reaction in the present embodiment is preferably 1 to 12 MPa, more preferably 1.2 to 9 MPa, still more preferably 1.5 to 5 MPa. With a reaction pressure of 1 MPa or more, a sufficient reaction rate can be obtained, so that the compound having a norbornene skeleton as a starting material tends to be prevented from remaining. With a reaction pressure of 12 MPa or less, no expensive facilities excellent in pressure resistance performance are required, so that economic advantage can be achieved. In particular, when the reaction is performed by a batch method or a semi-batch method, CO and $H_2$ are required to be discharged/depressed after completion of the reaction. With decrease in the pressure, the loss of CO and $H_2$ decreases, so that economic advantage can be achieved.

As the reaction method for the hydroformylation reaction in the present embodiment, a batch reaction method or a semi-batch reaction method is suitable. The semi-batch reaction is performed as follows. A solvent and, on an as needed basis, a rhodium compound and an organic phosphorus compound are added into a reaction vessel, and pressurization by CO and $H_2$ and heating, etc. are performed to provide the reaction conditions described above. The compound having a norbornene skeleton as a starting material or a solution thereof may be then supplied to the reaction vessel.

In the reaction products obtained in the hydroformylating step, the content of the compound represented by the following formula (3) is preferably 1 mol % or less, more preferably 0.7 mol % or less, still more preferably 0.5 mol % or less. In order to obtain the reaction products with a content in the range, each of the conditions of the hydroformylation reaction may be adjusted to preferable one as described above.

(3)

wherein $R_1$, $R_2$ and n are the same as defined in the formula (1).

In the reaction products obtained in the hydroformylating step, the conversion rate of the reactant is preferably 90% or more, more preferably 95% or more, still more preferably 99% or more. In order to obtain the reaction products with a conversion rate of the reactant in the range, each of the conditions for the hydroformylation reaction may be adjusted to preferable one as described above. The "conversion rate of the reactant" may be calculated from an equation: "((Monoolefin placed represented by formula (2)−Remaining monoolefin placed)/Monoolefin placed)×100%)", based on mass. More specifically, the method described in Examples is applied.

In the reaction product obtained in the hydroformylating step, the yield of the aldehyde is preferably 90% or more, more preferably 95% or more, still more preferably 99% or more. In order to obtain the reaction product with a yield of the aldehyde in the range, each of the conditions for the hydroformylation reaction may be adjusted to a preferable one as described above. The "yield of the aldehyde" may be calculated from an equation: "(Main product/Monoolefin placed, represented by formula (2)×100%)", based on mass. More specifically, the method described in Examples is applied.

The reaction product obtained by the hydroformylation reaction in the present embodiment may be subjected to purification by, for example, distillation, extraction, crystal precipitation, or the like. For example, the compound represented by the formula (3) may be removed by distillation purification with a low number of stages, so that the content of the compound represented by the formula (3) described above can be further adjusted within a range in which the effect of the present invention is not impaired.

The composition in the present embodiment may be any composition as long as it contains a bifunctional compound having a norbornane skeleton, and may further contain a compound having a norbornane skeleton or a compound represented by the formula (3).

The composition in the present embodiment may be a reaction product itself obtained in the hydroformylation reaction in the present embodiment, or may be a purified reaction product obtained in the hydroformylation reaction in the present embodiment.

The composition in the present embodiment can be used as coating additives, adhesives and starting materials of resin. For use as coating additives, adhesives and starting materials of resin, the composition may further contain a known base compound and an additive used for coating additives, adhesives and starting materials of resin, in addition to the bifunctional compound having a norbornane skeleton, the compound having a norbornane skeleton, and the compound represented by the formula (3).

The compound having a norbornene skeleton in the present embodiment is obtained by the production method in the present embodiment. The composition in the present embodiment also is obtained by the production method in the present embodiment.

EXAMPLES

The present embodiment is more specifically described with reference to Examples as follows, though the present embodiment is not limited to these Examples.

<Analysis Method>
1) Measurement Conditions for Gas Chromatography Analysis
Analytical instrument: Capillary gas chromatograph GG-2010 Plus manufactured by Shimazu Corporation
Analysis column: InertCap 1 (30 m, I.D.: 0.32 mm, film thickness: 0.25 µm) manufactured by GL Sciences Inc.
Oven temperature: 60° C. (0.5 min)–15° C./min-280° C. (4 min)
Detector: FID, temperature: 280° C.
2) Measurement Conditions for Inorganic Gas Analysis
Analytical instrument: Gas chromatograph GC-8A manufactured by Shimazu Corporation
Analysis column: WG-100 manufactured by GL Sciences Inc.
Oven temperature: 100° C.
Detector: TCD, temperature: 100° C.
3) Measurement Conditions for GC-MS
Analytical instrument: GCMS-QP2010 Plus, manufactured by Shimazu Corporation
Ionization voltage: 70 V Analysis column: DB-1 (30 m, I.D.: 0.32 mm, film thickness: 1.00 μm) manufactured by Agilent Technologies
Oven temperature: 60° C. (0.5 min)-15° C./min-280° C. (4 min)
4) Measurement Conditions for NMR
Instrument: JNM-ECA500 (500 MHz) manufactured by JEOL Ltd.
Measurement mode: 1H-NMR, 13C-NMR
Solvent: $CDCl_3$ (deuterated chloroform)
Internal standard substance: tetramethylsilane Example 1

In a 500-mL stainless steel reaction vessel, 173 g (2.01 mol) of methyl acrylate and 167 g (1.26 mol) of dicyclopentadiene were placed and reacted at 195° C. for 2 hours. A reaction liquid containing 96 g of monoolefin represented by the following formula (2a) acquired was subjected to distillation purification, and then a part of the purified product was supplied to a latter-stage reaction.

In a 300-mL stainless steel reaction vessel, a hydroformylation reaction of the monoolefin represented by the formula (2a) was performed. Into the reaction vessel, 30 g of the distillation-purified monoolefin represented by the formula (2a), 60 g of toluene (manufactured by Wako Pure Chemical Industries), 128 g (3000 molppm based on monoolefin) of triphenyl phosphite (manufactured by Wako Pure Chemical Industries), and 106 μg (3 molppm based on monoolefin) of Rh(acac) $(CO)_2$ (manufactured by N. E. Chemcat Corporation) were added. After the reaction vessel was purged with nitrogen three times, gas supply to the reaction vessel was performed with a molar ratio of CO to $H_2$ of 60:40 for a reaction at 100° C., 2 MPa. During the reaction, gas supply was performed such that the molar ratio of CO to $H_2$ in the reaction vessel was kept at 60:40. When the indicator value of the flow meter in the gas supply line reached 0, the supply of gas was stopped, and when the decrease in pressure in the reaction vessel stopped, the reaction was regarded as completed. After completion of the reaction, gas in the gas phase was collected to be subjected to gas composition analysis. Also, as a result of gas chromatography analysis, it was confirmed that the reaction liquid contained 33.3 g of the main product represented by the formula (1a), 0.2 g of the byproduct (hydrogenated product) represented by the formula (3a), and 0.0 g of the remaining monoolefin placed (conversion rate of reactant: 100.0% (=(monoolefin placed: monoolefin represented by formula (2a)–remaining monoolefin placed)/monoolefin placed)×100%), yield of aldehyde: 97.6% (=main product/monoolefin placed× 100%), yield of hydrogenated product: 0.7% (=hydrogenated product/monoolefin placed×100%)), (wherein, units other than % are based on mass). Also, as a result of GC-MS analysis, it was confirmed that the hydrogenated product represented by the formula (3a) had a molecular weight of 220 (value found by GC-MS instrument). For the molecular weight of each compound, the molecular weight of the monoolefin represented by the formula (2a) was regarded as 218.3, the molecular weight of the main product represented by the formula (1a) was regarded as 248.32, and the molecular weight of the hydrogenated product represented by the formula (3a) was regarded as 220.31, based on the atomic weight and isotopic ratio in the composition formula; thus, the conversion rate of the reactant, the yield of the aldehyde, and the yield of the hydrogenated product were calculated. The conversion rate of the reactant, the yield of the aldehyde, and the yield of the hydrogenated product were calculated based on amounts in moles.

(2a)

(1a)

(3a)

wherein Me represents a methyl group.

Examples 2 and 3, and Comparative Examples 1 and 2

A reaction liquid containing the compound represented by the formula (1a) and the compound represented by the formula (3a) was obtained from a reaction in the same manner as in Example 1, except that the molar ratio $CO/H_2$ in the reaction vessel was changed as shown in the following Table 1. The results of the conversion rate of the reactant and each of the yields are shown together in Table 1.

Example 4

In a 500-mL stainless steel reaction vessel, 173 g (2.01 mol) of methyl acrylate and 167 g (1.26 mol) of dicyclopentadiene were placed and reacted at 195° C. for 2 hours. A reaction liquid containing 198 g of monoolefin represented by the following formula (2b) acquired was subjected to distillation purification, and then a part of the purified product was supplied to a latter-stage reaction.

In a 300-mL stainless steel reaction vessel, a hydroformylation reaction of the monoolefin represented by the formula (2b) as reactant was performed. Into the reaction vessel, 30 g of the distillation-purified monoolefin represented by the formula (2b), 60 g of toluene (manufactured by Wako Pure Chemical Industries), 182 mg (3000 molppm based on monoolefin) of triphenyl phosphite (manufactured by Wako Pure Chemical Industries), and 153 μg (3 molppm based on monoolefin) of Rh(acac) $(CO)_2$ (manufactured by N. E. Chemcat Corporation) were added. After the reaction vessel was purged with nitrogen three times, gas supply to the reaction vessel was performed with a molar ratio of CO to $H_2$ of 60:40 for a reaction at 100° C., 2 MPa. During the reaction, gas supply was performed with the molar ratio of CO to $H_2$ in the reaction vessel kept at 60:40, so that a reaction liquid as product was obtained. After completion of the reaction, gas in the gas phase was collected to be subjected to gas composition analysis by inorganic gas analysis. Also, as a result of gas chromatography analysis of the reaction liquid, it was confirmed that the reaction liquid contained 34.7 g of the main product represented by the formula (1b), 0.16 g of the hydrogenated product represented by the formula (3b), and 0.0 g of the remaining monoolefin placed (conversion rate of reactant: 100.0%, yield of aldehyde: 96.6%, and yield of hydrogenated product: 0.5%). Also, as a result of GC-MS analysis, it was confirmed that the hydrogenated product represented by the formula (3b) had a molecular weight of 154 (value found by GC-MS instrument). For the molecular weight of each compound, the molecular weight of the monoolefin represented by the formula (2b) was regarded as 152.19, the molecular weight of the main product represented by the formula (1b) was regarded as 182.22, and the molecular weight of the hydrogenated product represented by the formula (3b) was regarded as 154.21, based on the atomic weight and isotopic ratio in the composition formula; thus, the conversion rate of the reactant, the yield of the aldehyde, and the yield of the hydrogenated product were calculated. The conversion rate of the reactant, the yield of the aldehyde, and the yield of the hydrogenated product were calculated based on amounts in moles.

wherein Me represents a methyl group.

Comparative Example 3

Figure 1:
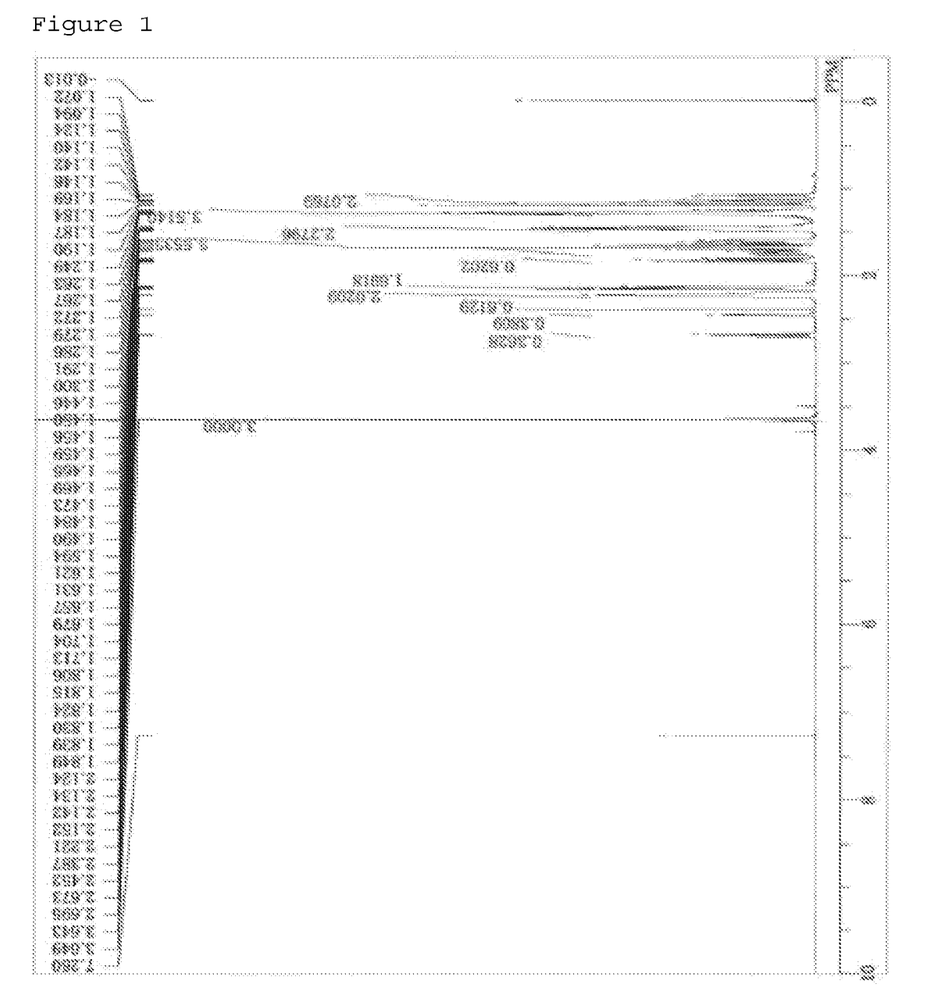
FIG. 1 shows a spectrum obtained through measurement of a byproduct obtained in Example 1 with 1H-NMR.
Figure 2:
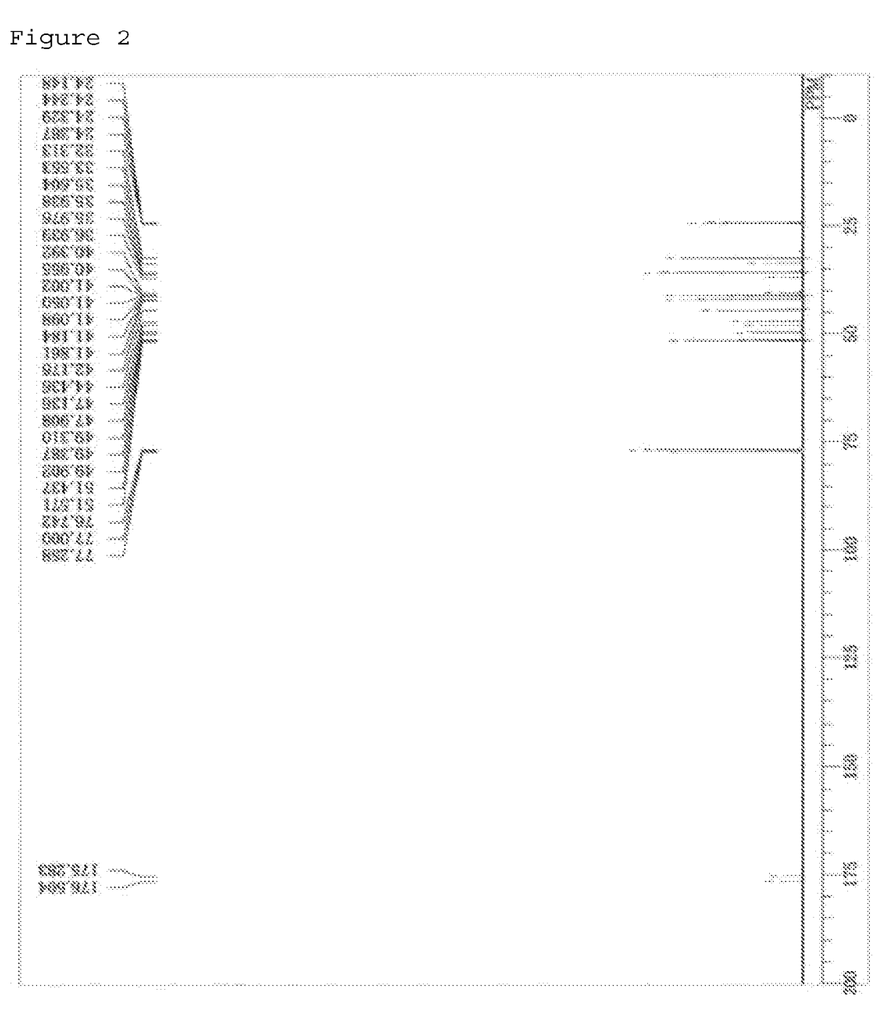
FIG. 2 shows a spectrum obtained through measurement of a byproduct obtained in Example 1 with 13C-NMR.

A reaction liquid containing the compound represented by the formula (1b) and the compound represented by the formula (3b) was obtained from a reaction in the same manner as in Example 4, except that the molar ratio CO/H$_2$ in the reaction vessel was changed as shown in the following Table 1. The results on the conversion rate of the reactant and each of the yields are shown together in Table 1.

obtained in Example 1, and FIG. 2 shows a spectrum obtained by 13C-NMR measurement of the byproduct obtained in Example 1. From the results of GC-MS analysis described above and NMR analysis in FIGS. 1 and 2, it was confirmed that the compound by-produced in Example 1 was a monofunctional compound represented by the formula (3a) described above.

Figure 3:
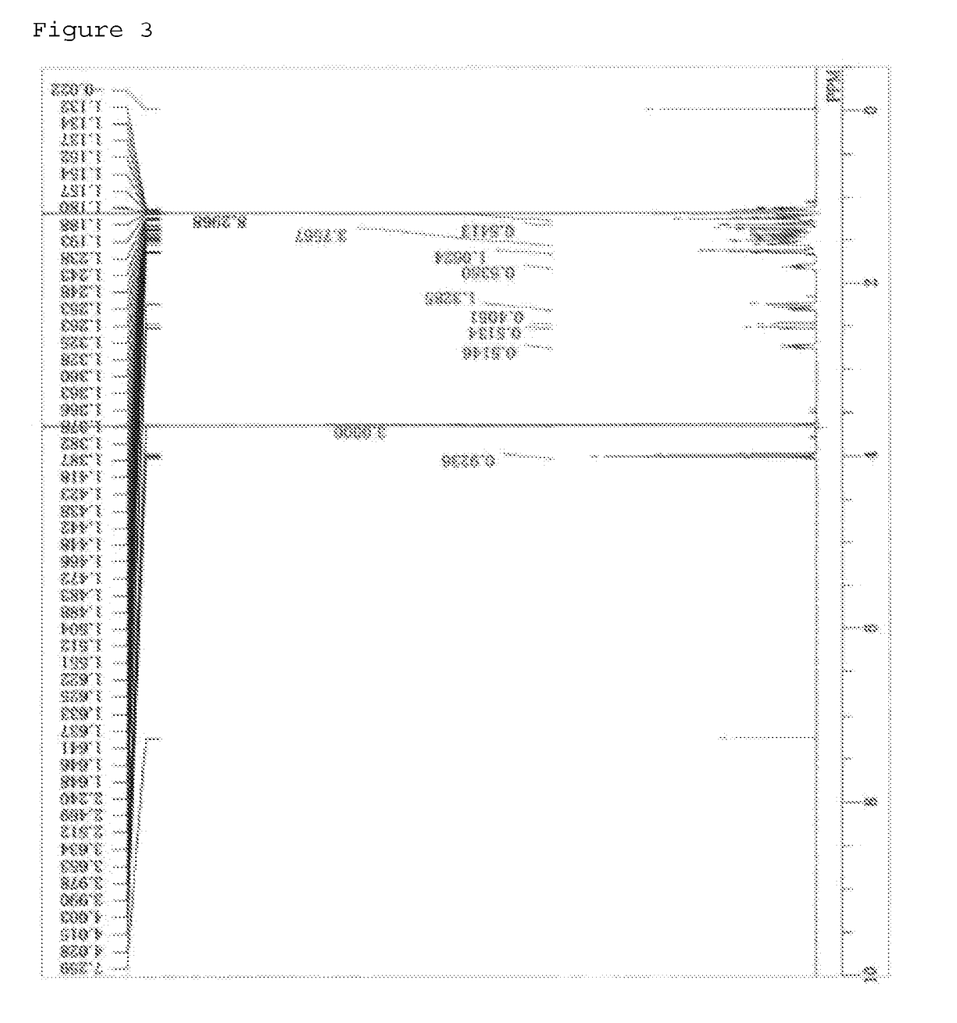
FIG. 3 shows a spectrum obtained through measurement of a byproduct obtained in Example 4 with 1H-NMR.
Figure 4:
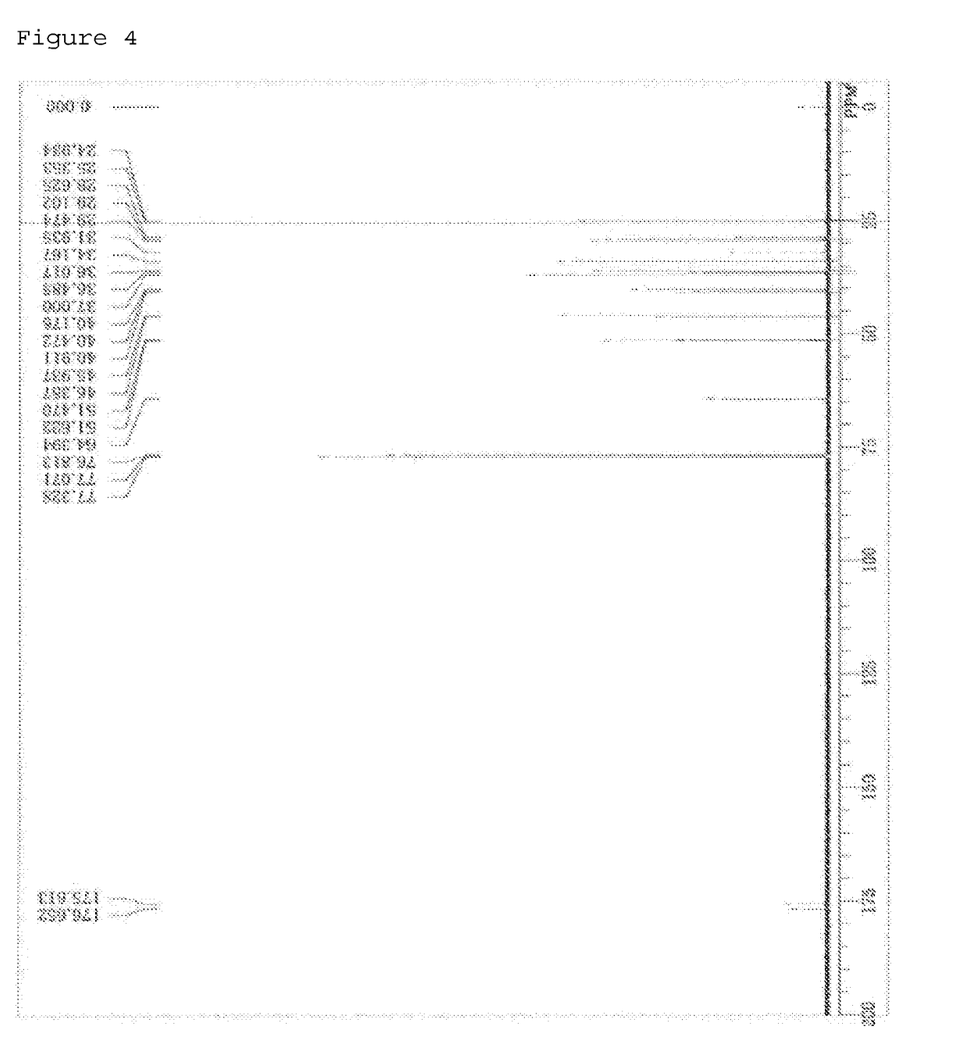
FIG. 4 shows a spectrum obtained through measurement of a byproduct obtained in Example 4 with 13C-NMR.

Also, the product obtained in Example 4 was subjected to NMR analysis. FIG. 3 shows a spectrum obtained in 1H-NMR measurement of the byproduct obtained in Example 4, and FIG. 4 shows a spectrum obtained in 13C-NMR measurement of the byproduct obtained in Example 4. From the results of GC-MS analysis described above and NMR analysis in FIGS. 3 and 4, it was confirmed that the compound by-produced in Example 4 was a monofunctional compound represented by the formula (3b) described above.

The present application claims priority to Japanese Patent Application No. 2018-115434 filed in Japan Patent Office on Jun. 18, 2018, the content of which is incorporated herein by reference.

INDUSTRIAL APPLICABILITY

The present invention has industrial applicability in the field of coating additives, adhesives, starting materials of resin and the like made from a bifunctional compound having a norbornane skeleton.

The invention claimed is:
1. A method for producing a compound of the following formula (1), the method comprising:
hydroformylating a compound of the following formula (2) with carbon monoxide and hydrogen,
wherein a molar ratio of the carbon monoxide to the hydrogen during the hydroformylating is from 70/30 to 95/5;

TABLE 1

|  |  | Example 1 | Example 2 | Example 3 | Comparative Example 1 | Comparative Example 2 | Example 4 | Comparative Example 3 |
|---|---|---|---|---|---|---|---|---|
| Temperature | [° C.] | 100 | 100 | 100 | 100 | 100 | 100 | 100 |
| Pressure | [MPa] | 2 | 2 | 2 | 2 | 2 | 2 | 2 |
| CO molar ratio | [%] | 60 | 70 | 80 | 50 | 40 | 60 | 50 |
| H2 molar ratio | [%] | 40 | 30 | 20 | 50 | 60 | 40 | 50 |
| Reaction time | [h] | 6 | 7.5 | 8 | 5 | 4 | 5 | 4 |
| Reactant type |  | 2a | 2a | 2a | 2a | 2a | 2b | 2b |
| Conversion rate of reactant | [%] | 100.0 | 99.9 | 100.0 | 99.9 | 100.0 | 100.0 | 100.0 |
| 10 Yield of aldehyde | [%] | 97.6 | 97.8 | 97.9 | 97.4 | 96.8 | 96.6 | 96.5 |
| Yield of hydrogenated product | [%] | 0.7 | 0.3 | 0.2 | 1.0 | 1.2 | 0.5 | 0.8 |
| CO/H2 ratio in gas phase after reaction (analysis value) | [vol %] | 1.65 | 2.91 | 4.36 | 1.04 | 0.62 | 1.23 | 0.82 |

<Identification of Product>

The byproduct obtained in Example 1 was isolated and subjected to NMR analysis. FIG. 1 shows a spectrum obtained by 1H-NMR measurement of the byproduct wherein:
R$_1$ is at least one selected from the group consisting of COOCH$_3$, COOC$_2$H$_5$, COOC$_3$H$_7$, COOC$_4$H$_9$, CHO, OCOCH$_3$, and OH;

$R_2$ is at least one selected from the group consisting of H, $CH_3$, and $C_2H_5$; and n is 0 or 1, (2)

2. The method of claim 1, wherein a reaction product of the hydroformylating comprises a compound of the following formula (3) at a concentration of 1 mol % or less:

(3)

3. The method of claim 1, wherein the hydroformylating uses from 0.1 to 60 micromoles of a rhodium compound per mole of the compound of the formula (2), and from 300 to 10,000 moles of an organic phosphorus compound per mole of a rhodium atom in the rhodium compound.

4. The method of claim 1, wherein the molar ratio of the carbon monoxide to the hydrogen during the hydroformylating is from 70/30 to 90/10.

5. The method of claim 1, wherein the molar ratio of the carbon monoxide to the hydrogen during the hydroformylating is from 70/30 to 80/20.

* * * * *